United States Patent [19]
Krueger et al.

[11] Patent Number: 6,045,530
[45] Date of Patent: Apr. 4, 2000

[54] ADJUSTABLE ANGLE CATHETER

[75] Inventors: John A. Krueger, Brookfield, Wis.;
Terry N. Layton, Long Grove, Ill.;
Demetrio Velez-Torres, Anasco, Puerto Rico

[73] Assignee: Heyer-Schulte NeuroCare Inc., Plainsboro, N.J.

[21] Appl. No.: 09/172,386

[22] Filed: Oct. 14, 1998

[51] Int. Cl.[7] .................................................. A61M 37/00
[52] U.S. Cl. .............................. 604/95; 604/524; 604/530
[58] Field of Search ............................ 604/523, 95, 528, 604/530, 94, 524

[56] References Cited

U.S. PATENT DOCUMENTS

| | | |
|---|---|---|
| 3,169,528 | 2/1965 | Knox, III et al. . |
| 3,805,300 | 4/1974 | Tascon-Alonso et al. ................ 623/13 |
| 4,033,331 | 7/1977 | Guss et al. . |
| 4,245,624 | 1/1981 | Komiya . |
| 4,435,174 | 3/1984 | Redmond et al. . |
| 4,596,564 | 6/1986 | Spetzler et al. ......................... 604/281 |
| 4,826,087 | 5/1989 | Chinery . |
| 4,898,577 | 2/1990 | Badger et al. . |
| 5,215,105 | 6/1993 | Kizelshteyn et al. ................... 128/898 |
| 5,391,146 | 2/1995 | That et al. . |
| 5,419,764 | 5/1995 | Roll . |
| 5,439,006 | 8/1995 | Brennen et al. . |
| 5,441,483 | 8/1995 | Avitall ...................................... 604/95 |
| 5,489,269 | 2/1996 | Aldrich et al. . |
| 5,489,270 | 2/1996 | van Erp . |
| 5,531,686 | 7/1996 | Lundquist et al. . |
| 5,588,964 | 12/1996 | Imran et al. . |
| 5,603,697 | 2/1997 | Grundy et al. . |
| 5,693,015 | 12/1997 | Walker et al. ............................. 604/96 |
| 5,738,666 | 4/1998 | Watson et al. .......................... 604/264 |

*Primary Examiner*—Ronald Stright
*Assistant Examiner*—Jerry Thissell
*Attorney, Agent, or Firm*—Skarsten Law Offices S.C.

[57] ABSTRACT

A catheter is provided which is disposed for insertion into a fluid-containing cavity of a patient, such as a ventricle of the patient's brain, to drain CSF therefrom. The catheter includes an elongated body provided with a cross-section having an outer surface which is smooth and free of projections, angles or the like which could damage adjacent brain tissue. The elongated body is further provided with proximal and distal ends, a first lumen disposed to serve as a fluid flow passage, and a second lumen extending past a given position located on the elongated body. A titanium wire element is inserted into the second lumen for enabling a neurosurgeon to readily select and adjust the angular orientation between first and second catheter segments, wherein the first and second segments comprise the portions of the elongated body extending between the given position and the proximal and distal ends, respectively. Reinforcing structure is provided around the elongated body to prevent an end of the wire from pushing or rupturing therethrough.

20 Claims, 3 Drawing Sheets

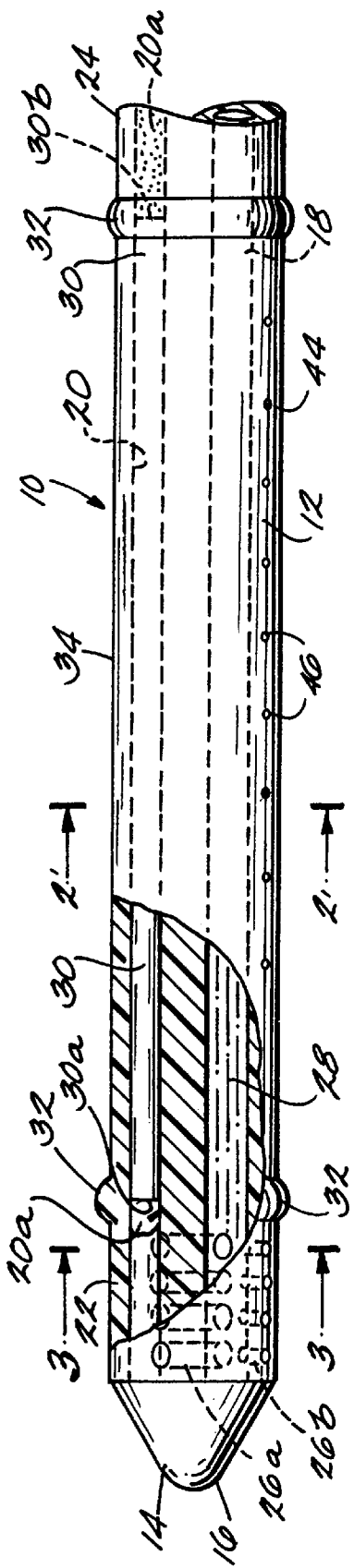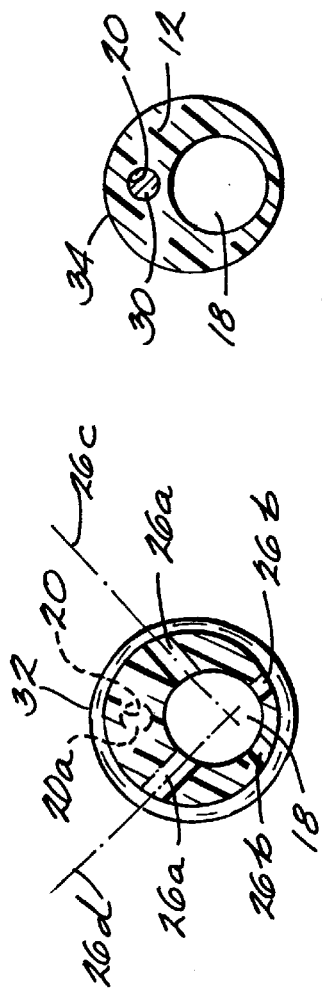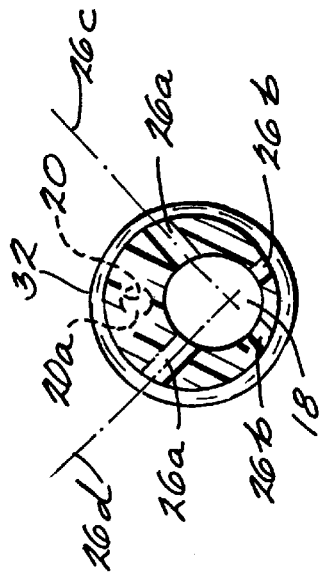

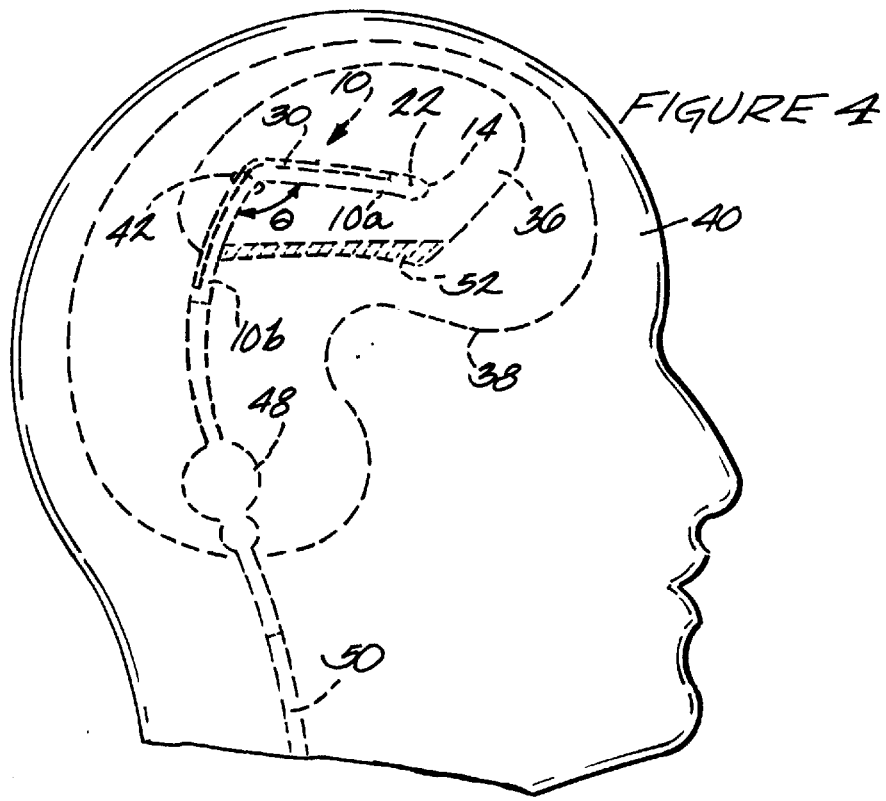
FIGURE 4
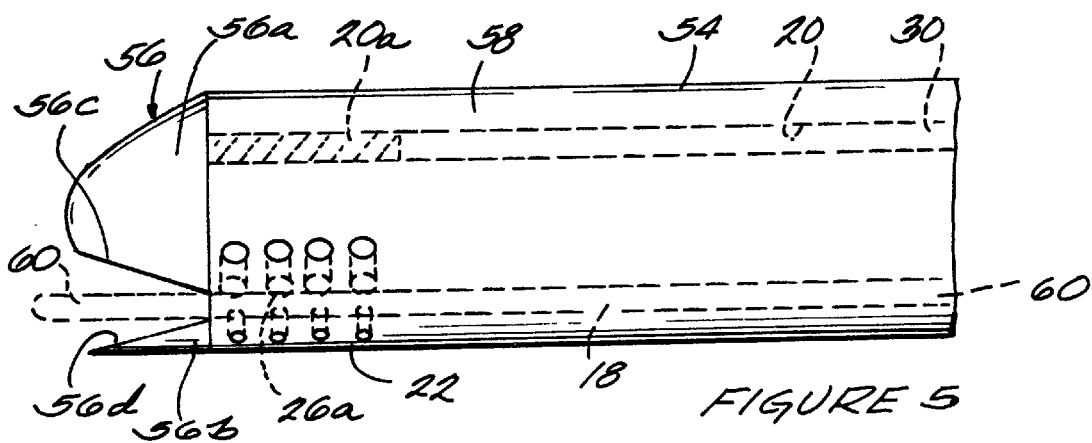
FIGURE 5
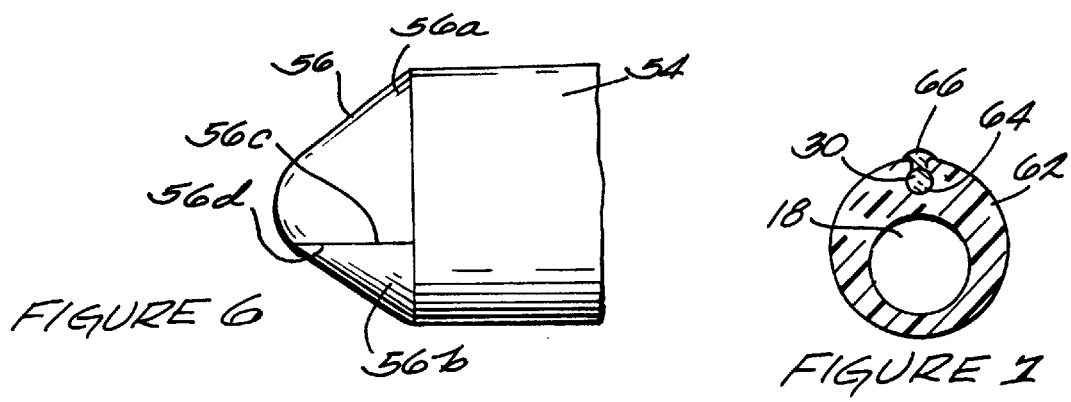
FIGURE 6
FIGURE 7

ADJUSTABLE ANGLE CATHETER

BACKGROUND OF THE INVENTION

The invention disclosed and claimed herein is generally directed to an improved catheter for implantation in a patient or other subject More particularly, the invention pertains to a catheter of such type which significantly simplifies the implantation procedure. Even more particularly, the invention pertains to a catheter of such type, wherein a bend of virtually any angle can be readily formed in the catheter, at any position along the length thereof.

As is well known, a shunt or shunt system can be implanted in a patient, in order to remove excess cerebrospinal fluid (CSF) from the patient's brain. The shunt system generally includes a ventricular catheter, comprising a thin tubular structure, which is inserted into a brain ventricle to provide a passage or channel for fluid flow. An implanted catheter usually must be able to remain in the brain on a long term or permanent basis, and is typically formed of pliable or resilient material such as silicone. In a common procedure for implanting a ventricular catheter, the surgeon bores a hole, sufficient to accommodate the catheter diameter, through the wall of the patient's skull. The catheter is then inserted through the hole by means of a stylet or the like. It is generally necessary to form or otherwise provide a bend in the catheter, proximate to the hole, so that the catheter portion extending out of the hole will lie along the patient's head. Such catheter portion can then be connected to a shunt valve or other component of the shunt system. Clearly, it is essential to avoid, as much as possible, traumatizing surrounding brain tissue during this procedure.

The bend which must be formed in the catheter will generally be of a fairly sharp angle, and lie in a range which may be on the order of 45°–90°. Since the catheter is formed of soft, pliable silicone, an angled bend of such magnitude could pinch or crimp the catheter and seriously obstruct fluid flow. To prevent such obstruction, a surgeon is provided with a set of different ventricular catheters, each having a specified angle preformed therein, at a specified distance from the proximal or forward end of the catheter. For example, some catheters in the set will have bends preformed therein at angles of 90°, and other catheters will have bends preformed therein at angles of 45°. The angled bends are located at standard distances from the proximal end of the catheter, such as at 5 centimeters, 7 centimeters and 9 centimeters therefrom. Such dimension is referred to herein as catheter insertion length. For a given implant operation, the neurosurgeon will select the catheter having the respective dimensions which he feels are most suited to a particular patient.

Unfortunately, with the present state of the art it may not be possible to accurately determine, in advance, the depth of insertion required for a catheter, in order to reach a particular ventricle. As a result, the insertion length of the catheter selected for use may be too long or too short. However, such deficiency will not become apparent until after the catheter has been inserted into a patient's brain. Since there is no way to adjust the location of a preformed bend along the length of a catheter, the inserted catheter must be withdrawn, and then replaced by another catheter having a longer or shorter insertion length, as required. It will be readily appreciated that withdrawal of the first catheter, followed by insertion of a second catheter, can significantly increase the trauma experienced by brain tissue proximate to the region of insertion. Moreover, since a surgeon using catheters with preformed bends is limited to standard sizes, both for bend angle and insertion length, he may not be able to fit a catheter to a patient as accurately as he would like.

An alternative prior art approach for providing a bend in a ventricular catheter is exemplified by U.S. Pat. No. 4,435,174, issued Mar. 6, 1984 to Redmond et al. Such patent is directed to structure for smoothly guiding a catheter around an arc, to provide bends of 90° or other prespecified angle. Such guides generally require stitches to affix them to a patient's scalp. Thus, additional steps are added to the shunt implantation procedure. Moreover, such guides once again have the disadvantage described above, i.e., they limit a surgeon to catheter bend angles of fixed standard sizes.

In view of the above drawbacks and disadvantages of the prior art, it would be desirable to provide an arrangement for forming a bend of any selected angle in a catheter, at any position along the length thereof. Moreover, the forward or proximal end of a conventional catheter, when inserted into a brain ventricle, may droop toward the floor or bottom thereof. This tends to bring the catheter drainage holes, through which CSF must pass, into contact with a substance known as chorid plexus. Such substance comprises fine strands or filaments, which can plug or clog the catheter drainage holes. Accordingly, it would be further desirable to provide rigidity to the proximal end of a catheter, to support it upwardly in the ventricle and away from the chorid plexus. Moreover, in an arrangement for a ventricular catheter, it is essential to avoid any projections, angles, or corners in the catheter outer surface. Any such projections or the like could tear or otherwise harm the surrounding brain tissue. It is particularly important to avoid such projections where the catheter is to remain in contact with delicate brain tissue for a long period of time. It is also essential to ensure that no hard internal component of the catheter, over the long period, is ever able to break or rupture through the smooth outer surface thereof.

SUMMARY OF THE INVENTION

The invention is generally directed to a catheter disposed for insertion into a fluid-containing cavity of a patient, such as a ventricle of the patient's brain, to drain fluid such as CSF therefrom. The catheter includes an elongated body provided with an outer surface having a circular cross-section. Thus, the outer surface of the catheter will be faired and smooth, and will be free of projections, angles or the like which could damage adjacent brain tissue. The elongated body is further provided with proximal and distal ends, a first lumen disposed to serve as a fluid flow passage, and a second lumen extending past a given position located on the elongated body. The catheter of the invention further includes a wire element means inserted into the second lumen for setting and maintaining a selected angular orientation between first and second body segments, wherein the first and second segments comprise the portions of the elongated body extending between the given position and the proximal and distal ends, respectively. The catheter further comprises means positioned in proximate relation to at least the forward end of the wire element, to constrain such forward end against movement outwardly, through the outer surface of the elongated body.

In a preferred embodiment of the invention, the elongated body is formed of selected pliable material, such as silicone, and the catheter is provided with a tip which is joined to the elongated body at its proximal end. The wire element means comprises a malleable wire element, usefully formed of titanium, which has an end oriented toward the proximal end of the catheter. The means for constraining movement of the forward end of the wire element comprises a ring of reinforcing material which is positioned around the outer surface of the elongated body, so as to surround the forward end of the wire element. Preferably also, the elongated body includes a proximal end region extending between the end of the wire element and the proximal end of the body, the first lumen extending into the proximal end region. A set of drainage holes are formed through the proximal end region, in communication with the first lumen.

In another embodiment of the invention, the wire element means comprises a plurality of wire elements, each being of reduced diameter and extending along the elongated body in its own lumen. The plurality of wire elements act collectively to enable a user to establish, maintain, and selectively adjust the angular orientation between the first and second body segments.

OBJECTS OF THE INVENTION

An object of the invention is to provide an improved catheter for use in connection with a shunt, to drain excess CSF from a ventricle or other cavity of a patient.

Another object is to provide a malleable catheter of the above type which enables a user thereof to form a bend of any desired angle in the catheter, at virtually any position along the length thereof, without interfering with fluid flow therethrough.

Another object is to provide a catheter of the above type which is intended for placement in a patient's brain on a permanent or long-term basis.

Another object is to provide a catheter of the above type intended to reside in a patients' brain on a permanent or long-term basis, wherein safety is significantly enhanced.

Another object is to provide a catheter of the above type which significantly reduces trauma caused to surrounding brain tissue, both during initial insertion and during the period the catheter remains in place within the patient.

Another object is to provide a catheter of the above type, wherein the position of the catheter within a patient can be readily detected by means of X-ray and fluoroscopy techniques.

Another object is to provide a catheter of the above type which includes markings or indicia for enabling a neurosurgeon to readily determine the depth to which the catheter has been inserted into a patient.

Another object is to provide a catheter of the above type, wherein clogging of fluid drain passages by chorid plexus is significantly reduced.

These and other objects of the invention will become more readily apparent from the ensuing specification, taken together with the accompanying drawings.

BRIEF DESCRIPTION OF THE DRAWINGS

FIG. 1 is a perspective view, with a section broken out, showing an embodiment of the invention.

FIG. 2 is a sectional view taken along lines 2—2 of FIG. 1.

FIG. 3 is a sectional view taken along lines 3—3 of FIG. 1.

FIG. 4 is a view showing the embodiment of FIG. 1 in use.

FIG. 5 and 6 are perspective views showing a modification of the embodiment shown in FIG. 1.

FIG. 7 is a sectional view showing a second modification of the embodiment shown in FIG. 1.

DETAILED DESCRIPTION OF THE PREFERRED EMBODIMENT

Figure 9:
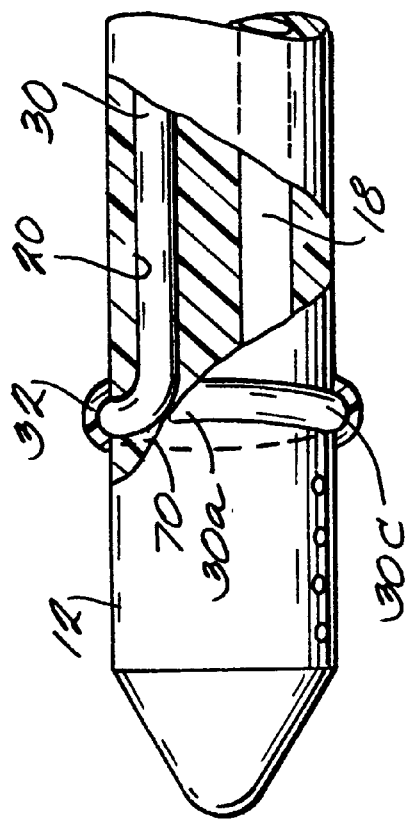
FIG. 9 is a perspective view, with a section broken out, showing a fourth modification of the embodiment shown in FIG. 1.

Referring to FIG. 1, there is shown a catheter 10 constructed in accordance with the principles of the invention. Catheter 10 is considered to be well suited for use in a shunt system as a ventricular catheter, i.e., as the shunt component which is inserted into a brain ventricle to carry CSF therefrom to a shunt valve or the like. However, it is also anticipated that catheter 10 could be used to drain excess fluid from a spinal or other cavity. Catheter 10 is provided with an elongated body 12, comprising a tubular structure, formed of soft pliable material such as silicone. Such material generally is biocompatible. Also, such material is comparatively inert, and will not degrade or decompose if it resides in the brain on a long term basis, which may be on the order of years. The outer diameter of elongated body 12, i.e., the diameter of catheter 10 is on the order of 0.10–0.125 inches.

To make the catheter insertion process easier, and to minimize tearing of brain tissue, catheter 10 is provided with a tip 14, having a slightly rounded point 16, which is joined to the silicon body 12 at the proximal end of the catheter, i.e., at the left end thereof as viewed in FIG. 1. Tip 14 is preferably formed of a tantalum silicone mixture. Such material can be ground to form the point 16. Also, it is stiff enough to urge brain tissue out of its path as the catheter 10 is being inserted therethrough. The tantalum tip will be readily viewable by means of X-ray or fluoroscopy. Accordingly, the location of the proximal end of catheter 10 can be readily determined when it is residing within a patient. A lubricious and/or antibiotic coating may be applied to the surface of elongated body 12.

Referring to FIG. 1 together with FIG. 2, there are shown two lumens, or ducts, 18 and 20 formed in elongated body 12. Lumen 18, having a diameter on the order of 0.05 inches, extends from the proximal end of catheter 10 to the distal end thereof, i.e., from the left end to the right end thereof as viewed in FIG. 1. Lumen 20, having a diameter on the order of 0.025 inches–0.03 inches, likewise extends along the entire length of catheter 10. Catheter 10 includes proximal and distal end regions 22 and 24, respectively, comprising portions of the elongated body 12 which are approximately 1 and one quarter inches in length, and respectively extend from the proximal and distal ends of the catheter. The portions of lumen 20 lying within regions 22 and 24 are filled with a material 20a, known as RTV, which hardens into silicone. Usefully, the lubricious coating referred to above is also placed on the walls of lumens 18 and 20.

FIG. 1, together with FIG. 3, shows a number of rows of drainage holes 26a and 26b formed through proximal end region 22, between the outer surface of elongated body 12 and lumen 18. Thus, when catheter 10 is inserted into a brain ventricle, CSF 28 can flow through drainage holes 26a and 26b into lumen 18, and therethrough to a shunt valve or other shunt component coupled to the distal end of catheter 10, as described hereinafter in connection with FIG. 4. In one embodiment, drainage holes 26a and 26b have diameters on the order of 0.03 inches and 0.02 inches, respectively, so that holes 26a are significantly larger than holes 26b. As shown by FIG. 3, each hole 26a lies along an axis 26c or 26d, in coaxial relationship with a hole 26b and in opposing relationship therewith across lumen 18. A pair of axes 26c and 26d are usefully oriented at approximately 90° with respect to one another.

Referring further to FIG. 1, there is shown a titanium wire 30 inserted into lumen 20, in snug fitting relationship therewith and taking up virtually all the space therein, except for the portions filled with RTV 20a When catheter 10 has been implanted in a patient's brain, the titanium wire 30 will show up very well in X-ray brain images. Thus, wire 30 as well as tantalum tip 14 provide very useful means for determining the precise location of an implanted catheter. Moreover, the titanium wire is generally free of ferrous impurities. Accordingly, it will not create a hazard in a magnetic resonance imaging (MRI) procedure.

FIG. 1 further shows a silicone reinforcing ring 32 positioned around the outer circumference of elongated body 12, adjacent to, that is, at the same position along the length of elongated body 12, as the proximal end 30a of wire 30. Reinforcing ring 32 is provided as an important safety measure, to substantially reduce the chance that the end 30a of the wire 30, at some time during the long period which it resides in the patient, will rupture through the silicone of body 12 and injure surrounding brain tissue. A similar ring, if desired, can be placed around body 12 adjacent to distal end 30b of wire 30.

Referring further to FIGS. 2 and 3, it is seen that the outer circumference or boundary 34 of elongated body 12 is circular. Such configuration further enhances the safety of catheter 10. Projections along the outer surface of catheter 10, as well as structures having angles or corners which could potentially tear sensitive brain tissue, are thereby eliminated from the outer surface of catheter 10. FIGS. 2 and 3 also show lumen 18 having a circular cross section, to enable it to be readily connected to a shunt valve or other conventional shunt component. Lumen 20 may have a circular, semi-circular or other cross sectional configuration.

Referring to FIG. 4, there is shown the catheter 10 inserted into a ventricle 36, located in the brain 38 of a patient 40. More specifically, a forward or proximal segment 10a of the catheter is inserted through a hole 42 formed through the patient's skull. The remainder of the catheter, comprising a distal segment 10b, must be bent to an angle θ with respect to segment 10a, so that distal segment 10b will lay along the outside of the patient's skull, and be oriented downwardly with respect thereto. It is to be understood that titanium wire 30 is initially in a substantially straight or linear configuration. Accordingly, a neurosurgeon can readily insert catheter 10 directly through the hole 42 and into brain 38 by means of a stylet or the like. When tip 14 reaches ventricle 36, the neurosurgeon will form a bend in the titanium wire, of angle θ, at a position along the catheter which is proximate to hole 42. Because the wire 30 extends along nearly the entire length of catheter 10, the location of the bend is determined solely by the length which catheter segment 10a must have in order to reach ventricle 36 from hole 42. There is thus no constraint placed on the insertion length of the catheter, which would be the case if the catheter had a preformed bend therein, as described above. Moreover, the titanium wire 30 can be bent to any angle desired by the neurosurgeon. At the same time, the bend in the wire will be smooth enough to prevent crimping or obstruction of fluid flow through the lumen 18.

Referring further to FIG. 1, there are shown markings or indicia 44 and 46, comprising large and small black dots, respectively, which are placed along the exterior surface of catheter 10. Large dots 44 are usefully located at distances of 5 centimeters and 10 centimeters from the end of tip 14, and small dots 46 are located at distances of 4, 6, 7, 8 and 9 centimeters therefrom. Such markings are very helpful to the neurosurgeon in properly locating catheter 10 within the patient's brain.

Referring further to FIG. 4, there is shown distal catheter segment 10b, as well as lumen 18 passing therethrough, coupled to the inflow side of a pressure responsive shunt valve 48. Valve 48 comprises a device well known in the brain shunt field, and is provided with a preset pressure rating. The inter-cranial pressure (ICP) of CSF in ventricle 36 is applied to valve 48 through CSF in lumen 18. When such pressure exceeds the preset rating, the valve opens, allowing CSF to flow into a catheter 50, such as a peritoneal catheter, which drains the fluid into the patient's stomach region (not shown). It is to be noted that catheter segment 10b, valve 48, and catheter 46 are respectively represented in FIG. 4 by means of dashed lines. This is because such components are typically implanted subcutaneously in a patient, and are accordingly hidden from view.

FIG. 4 further shows the portion of titanium wire 30 which extends along catheter segment 10a providing sufficient rigidity to keep the proximal region 22 of catheter 10 from drooping down into the chorid plexus 52 located along the floor of ventricle 36. By keeping region 22 away from the chorid plexus, wire 30 substantially reduces the chance that the chorid plexus will, over time, block drainage holes 26a and 26b of catheter 10.

Referring to FIG. 5, there is shown a modification of the invention comprising a catheter 54. Catheter 54 is very similar to catheter 10, and is shown to generally include the same components. However, a slit tip 56 has been substituted in catheter 54 for the solid or bullet tip 14 of catheter 10. Catheter tip 56 comprises two tip components 56a and 56b, both formed of tantalum silicone mixture and provided with flat, planar surfaces 56c and 56d, respectively. Components 56a and 56b are joined to silicone catheter body 58, which tends to urge the components 56a and 56b together, so that the surfaces 56c and 56d are in abutting relationship as shown in FIG. 6. When catheter 54 is in such mode, tip 56 serves to enhance insertion of catheter 54 into a brain cavity, as described above. However, once a catheter 54 is in place, a 1.2 mm outer diameter endoscope may be inserted through the lumen 18 of catheter 54, the lumen extending to the joint between tip components 56a and 56b. The endoscope 60 is advanced as the distal end of catheter 54 is held in place, so that the forward tip of endoscope 60 spreads the components 56a and 56b apart and passes between them, as shown in FIG. 5. Endoscope 60 comprises a currently available device, such as a 1.2 mm Neuro View Endoscope manufactured by Neuro Navigational, which has a light source and fiber optic path for camera imaging located in its tip. Thus, endoscope 60 may be used to view the cavity into which catheter 54 has been placed. Thereafter, endoscope 60 is withdrawn, and tip components 56a and 56b are urged back into abutting relationship as shown in FIG. 6.

Referring to FIG. 7, there is shown a catheter 62, wherein a groove 64 has been substituted for the lumen or closed passage 20, which is to receive the titanium wire 30. After a wire 30 has been placed along the groove 64, the wire is sealed in place in the groove by silicone material 66. The edges of the material 66 are feathered, to ensure a smooth external surface of catheter 62.

Figure 8:
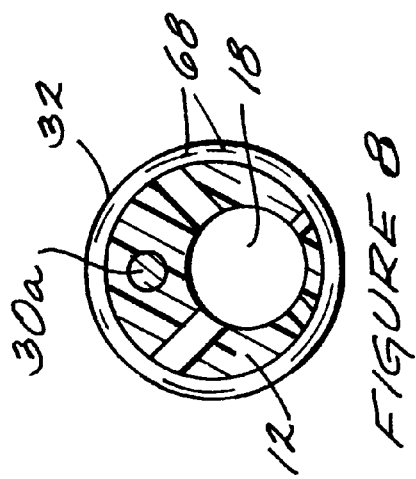
FIG. 8 is a sectional view showing a third modification of the embodiment shown in FIG. 1.

As stated above, it is very important to prevent an end 30a or 30b of wire 30 from pushing through elongated body 12. Accordingly, referring to FIG. 8, there is shown a further measure to retain such wire ends within body 12. As depicted therein, strands 68, formed of material such as dacron, are placed in each reinforcing ring 32 to surround body 12. Dacron strands 68 provide a substantial amount of additional reinforcing for the rings 32.

Referring to FIG. 9, there is shown an alternative arrangement to prevent a sharp edge of end 30a of wire 30 from coming into contact with surrounding brain tissue. In accordance therewith, a forward portion 30c of wire 30 passes outward from lumen 20, through an aperture 70 formed between the forward or proximal end of lumen 20 and the outer surface of elongated body 12. Forward wire portion 30c is formed into a tight loop around the outer surface of body 12. The end 30a of wire 30, and any sharp edge thereon, is thereby held in tight, abutting relationship against another portion of the wire 30. A reinforcing ring 32, as described above, is placed around the wire loop. A similar loop may be formed in the rearward end of wire 30, with respect to end 30b thereof.

Because wire 30 is a thin, elongated piece of metal, it tends to act as a spring when a bend is formed therein, as described above in connection with the use of the catheter 10 in a patients' brain. Thus, tension or potential energy may be stored in the bent wire 30, and may remain therein for a long period of time. This tension, acting on the portion of wire 30 included in proximal catheter segment 10a, may eventually urge the end 30a to rupture through silicone body 12.

Figure 10:
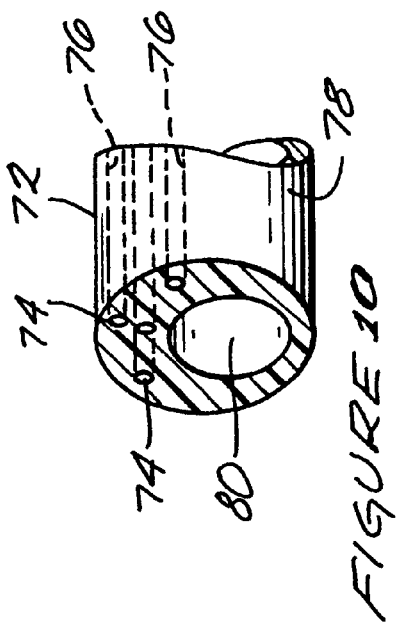
FIG. 10 shows a section of a fifth modification of the embodiment shown in FIG. 1.

To significantly reduce the possibility of such occurrence, FIG. 10 shows a catheter 72, comprising a modification of the invention, which, employs a plurality of wires 74 rather than the single wire 30 described above. Usefully, there are two or three of such wires 74, each contained in its own lumen 76. Catheter 72 includes a silicone body 78, similar to body 12, which has a lumen 80 formed through it for draining fluid. Each wire 74 has a diameter such as 0.01 inches–0.015 inches, which is substantially less than the diameter of wire 30, and the wires 74 are spaced apart from one another around the circumference or outer surface of body 78. Since there are a plurality of wires 74, they are, collectively, as effective in setting and maintaining a bend of angle θ in catheter 10, described above, as the single wire 30. However, because each wire 74 is of much smaller diameter, the amount of tension which can be stored in an individual wire 74 is significantly less than can be stored by a wire 30. Moreover, by spacing the wires 74 apart from one another, the tension or potential energy which is collectively stored thereby is distributed over a substantial portion of the silicone body 78 of catheter 72, rather than concentrated at a single location, as is the case with the single wire 30. As a result, it becomes much less likely that a single wire 74 will be under sufficient force to rupture through the silicone body 78 of the catheter 72.

Obviously, many other modifications and variations of the present invention are possible in light of the above teachings. It is therefor to be understood that within the scope of the disclosed concept, the invention may be practiced otherwise than as has been specifically described.

What is claimed is:

1. A catheter disposed for insertion into a fluid-containing cavity of a patient to drain fluid therefrom, said catheter comprising:

an elongated body provided with proximal and distal ends and with an outer surface having a circular cross-section, said elongated body being further provided with first and second lumens contained within said outer surface and extending along said body, said first lumen disposed to serve as a fluid flow passage and said second lumen being proximate to a position on said elongated body determined by the depth to which said catheter is inserted into said cavity;

a wire element inserted into said second lumen for establishing and maintaining a selected angular orientation between first and second segments of said elongated body, said first and second segments comprising the portions of said elongated body extending between said position and said proximal and distal ends, respectively; and an annular retaining structure of selected material positioned around said elongated body and surrounding said proximal end of said wire element, to retain said wire element within said elongated body.

2. The catheter of claim 1 wherein:

said wire element comprises a specified length of malleable wire located in said second lumen.

3. The catheter of claim 2 wherein:

said annular retaining structure comprises a ring of reinforcing material positioned around said outer surface of said elongated body.

4. The catheter of claim 3 wherein:

dacron strands are placed in said ring of reinforcing material to surround said elongated body and to further strengthen said ring.

5. The catheter of claim 2 wherein:

said annular retaining structure comprises a segment of said malleable wire which is joined in integral relationship to an end of said length of wire, said wire segment passing outward from said second lumen and being formed into a loop around said outer surface of said elongated body so that an end of said wire segment is held in tight abutting relationship with another portion of said malleable wire.

6. The catheter of claim 1 wherein:

said catheter includes a plurality of said second lumens which extend along said elongated body, and are spaced apart from one another along said outer surface of said elongated body; and said wire element comprises a specified length of malleable wire located in each of said second lumens.

7. The catheter of claim 2 wherein:

said elongated body includes a proximal end region extending between said end of said wire element and said proximal end of said body;

said first lumen extends into said proximal end region; and a set of drainage holes are formed through said proximal end region between said first lumen and the outer surface of said elongated body.

8. The catheter of claim 7 wherein:

reference indicia are placed along said elongated body at prespecified distances from said proximal end.

9. The catheter of claim 2 wherein:

said catheter further comprises a tip joined to said elongated body at said proximal end.

10. The catheter of claim 9 wherein:

said tip comprises a bullet tip formed of tantalum.

11. The catheter of claim 9 wherein:

said catheter is disposed for use with an endoscope having a probe, and said tip comprises a slit tip disposed to allow said probe to selectively pass therethrough.

12. The catheter of claim 2 wherein:

the diameter of said circular cross-section is no greater than one-eighth inch.

13. A catheter disposed for insertion into a fluid-containing cavity of a patient to drain fluid therefrom, said catheter comprising:

an elongated body provided with an outer surface and with proximal and distal ends, said elongated body being further provided with a first lumen and with a selected number of second lumens, each of said lumens being contained within said outer surface and extending along said body, said first lumen disposed to serve as a fluid flow passage, and each of said second lumens being proximate to a position on said elongated body determined by the depth to which said catheter is inserted into said cavity;

a wire element inserted into each of said second lumens for establishing and maintaining a selected angular orientation between first and second segments of said elongated body, said first and second segments comprising the portions of said elongated body extending between said position and said proximal and distal ends, respectively; and an annular retaining structure of selected material positioned around said elongated body and surrounding said proximal end of said wire element, in order to retain said wire element within said elongated body.

14. The catheter of claim 13 wherein:

said elongated body is provided with a plurality of said second lumens which are spaced apart from one another along the outer surface of said elongated body; and said wire element means comprises a specified length of malleable wire located in each of said second lumens.

15. The method of claim 13 wherein:

said elongated body is provided with a single one of said second lumens.

16. The catheter of claim 15 wherein:

said wire element comprises a specified length of malleable wire located in said second lumen.

17. The catheter of claim 16 wherein:

said annular retaining structure comprises a ring of reinforcing material positioned around said outer surface of said elongated body.

18. The catheter of claim 17 wherein:

dacron strands are placed in said ring of reinforcing material to surround said elongated body and to further strengthen said ring.

19. The catheter of claim 16 wherein:

said annular retaining structure comprises a segment of said malleable wire which is joined in integral relationship to an end of said length of wire, said wire segment being passed outward from said second lumen and formed into a loop around said outer surface of said elongated body so that an end of said wire segment is held in tight abutting relationship with another portion of said malleable wire.

20. The catheter of claim 13 wherein:

the outer surface of said elongated body has a circular cross-section the diameter of said circular cross-section being no greater than one-eighth inch.

* * * * *